United States Patent [19]

Naggiar

[11] Patent Number: 4,923,478

[45] Date of Patent: May 8, 1990

[54] COSMETIC STICK COMPOSITION

[75] Inventor: Samir F. Naggiar, East Windsor, N.J.

[73] Assignee: Carter-Wallace, Inc., New York, N.Y.

[21] Appl. No.: 231,305

[22] Filed: Aug. 11, 1988

[51] Int. Cl.$^5$ .............................................. A61K 7/155
[52] U.S. Cl. ........................................ 8/161; 424/72; 424/70; 132/202
[58] Field of Search ................... 8/94.16, 161; 424/72, 424/70; 132/202

[56] References Cited

U.S. PATENT DOCUMENTS

| 1,982,268 | 11/1934 | Roth et al. | 8/161 |
| 2,487,558 | 11/1949 | Kamlet | 8/94.16 |
| 3,194,736 | 7/1965 | Braun et al. | 8/161 |
| 3,426,137 | 2/1969 | Philpitt et al. | 8/161 |
| 4,121,904 | 10/1978 | Schamper | 8/161 |
| 4,401,663 | 8/1983 | Buckwalter et al. | 8/161 |
| 4,546,112 | 10/1985 | Lattann et al. | 8/161 |
| 4,631,064 | 12/1986 | Juneja | 8/161 |

Primary Examiner—A. Lionel Clingman
Assistant Examiner—Helene Klemanski
Attorney, Agent, or Firm—Kevin B. Clarke

[57] ABSTRACT

Solid cosmetic stick-type depilatory compositions consisting essentially of sodium stearate, propylene glycol, water, sodium hydroxide solution and thioglycolic acid salts as the essential active depilating agent are disclosed.

3 Claims, No Drawings

COSMETIC STICK COMPOSITION

COSMETIC STICK COMPOSITION

The present invention is directed to cosmetic stick-type compositions. More particularly, the invention is concerned with stick-type depilatory compositions. Specifically, the present invention relates to hydrous stick depilatory compositions.

BACKGROUND

The use of cosmetic compositions in stick form is well known. Lipsticks have been an item of women's toilet for more than one hundred years. In addition, a substantial commercial enterprise has been built in fairly recent times in the area of deodorant and antiperspirant stick compositions.

Depending upon the specific intended function of the stick, the principal vehicle employed in the formation of the stick composition will be found to be widely varied, i.e., U.S. Pat. No. 4,226,889 discloses cosmetic stick compositions, i.e., deodorant, perfume, sun, humectant, lanolin, hand lotion, talc, pigment and insect repellant stick formulations which comprise sodium stearate, water and active ingredient. In addition, stick-type deodorant compositions typically consist of bacteriostat or other biologically active compound dispersed in a vehicle comprising an alcohol-based gel containing either ethanol or glycol such as propylene glycol, as the vehicle base. In either case, gelation is effected by use of soap, e.g., sodium stearate, as the gelling agent. These stick-type deodorants may also contain small amounts of other additives, such as perfumes, humectants, various surfactants, dyes or other colorants, water, etc. Both types of formulation have left something to be desired. For example, the ethanol in the ethanol-based product is relatively volatile and can evaporate on storage, especially, at elevated temperatures. As a consequence, the stick shrinks and becomes mis-shapen and generally useless. The glycol-based deodorant sticks do not suffer from this disadvantage; however, glycols provide a product which is hard and waxy and thus has an undesirable "feel" and/or little covering power.

Lipsticks and similar cosmetic products, on the other hand, typically employ fats and/or waxes, such as castor oil, carnauba wax, candelia wax, beeswax, and the like. Vehicles of this type are relatively expensive, and in many cases cannot be employed in the formulation of other cosmetic products.

Powder sticks have been formed by compression of the powder; however, such products are generally so hard that it is difficult to deposit sufficient powder when the compressed Powder is applied to the skin of the user. As a consequence, various solutions have been proposed, such as reducing the degree of compression, coupled with providing the composition with a separate wrapper or a dry film to prevent "shedding" of the loosely compacted powder. See, e.g., U.S. Pat. No. 3,471,611. In another effort, the use of gums or other materials as adhesive binders have been described in U.S. Pat. No. 3,800,034. Such efforts have not been particularly successful, and by increasing the number of manufacturing steps, necessarily increase cost of manufacture of the product.

Additional wax and soap sticks are disclosed in numerous United States Patents, i.e., U.S. Pat. Nos. 4,414,200; 4,383,988; 4,382,079; 4,280,994; 4,265,878; 3,259,545; 2,970,083; 2,933,433; 2,900,306 and 2,857,315.

Depilatories in the form of anhydrous depilatory compositions in solid stick form containing as the essential active depilating agent a substituted thiol in which the hydrogen atom in hydrogen sulfide is substituted by various organic residues are disclosed in U.S. Pat. No. 3,194,736.

SUMMARY OF THE INVENTION

It is an object of the present invention to provide an improved cosmetic stick composition.

It is yet another object of this invention to provide a hydrous stick depilatory composition unique in its formulation.

It is a further object of the present invention to provide a hydrous stick depilatory composition which is soft enough to react readily when applied to the wetted skin yet sufficiently hard to provide a stable stick product.

A still further object of this invention is the production of clear, stable stick depilatory compositions.

These and other objects of this invention, which will be apparent to those skilled in the art from the ensuing specification and claims are achieved through the production of a solid depilatory composition which consists essentially of a sodium stearate dispersion in admixture with propylene glycol, water, thioglycolate salts and an alkali solution sufficient to maintain the pH of the system above about 12 while depilating on wet skin.

The basic vehicle of the composition of the present invention is the combination of water, propylene glycol and sodium stearate in proportions to form a self-supporting solid composition which does not readily deform yet is not so firm and hard that it will not leave a sufficient deposit, i.e., about a 10% solution of active ingredient when applied to wetted skin.

As a general rule compositions meeting the aforesaid criterion are obtained when the proportion of sodium stearate is in the range of from about 6% to about 12% by weight of the total composition about 15% to about 60% by weight of water, preferred compositions contain about 9% by weight of sodium stearate per about 27% to about 42% by weight water. The proportion of propylene glycol to sodium stearate likewise ranges from about 15% to about 60% propylene glycol per about 9% by weight sodium stearate preferably about 33% to about 45% by weight propylene glycol per about 9% by weight sodium stearate.

The fourth essential component of the solid compositions of the present invention is the active ingredient, the thioglycolate acid salts such as sodium, calcium and potassium and mixtures thereof in a concentration of from about 4% to about 8% by weight, preferably from about 5% to about 6.5% by weight. The thioglycolate acid salt may be added per se to the composition or prepared in situ by reacting thioglycolic acid with the appropriate alkali, i.e., calcium hydroxide, sodium hydroxide. Further, sufficient excess of such alkali is present in the compositions in order to maintain the pH of the compositions above about pH 12, preferably a pH of between about 12.25 and 12.50 is maintained.

The hydrous solid stick compositions of the present invention may optionally contain ingredients suitable for improving efficacy, stability, cosmetics and/or aesthetics. Such optional ingredients include deodorant materials, perfumes, pigments, dyes coloring agents and the like. Particularly preferred optional components are non-ionic emulsifying agents such as conventionally used in depilatory compositions which are the reaction products of saturated higher fatty alcohols such as stearyl, lauryl, cetyl alcohol and mixtures thereof with ethylene or propylene oxide. One such material is the trademark product BRIJ 30 sold by I.C.I. Corporation.

DETAILED DESCRIPTION OF THE INVENTION

The compositions of the present invention may be prepared by batch processing, however, in the preferred embodiment, the order and method of addition of the ingredients of the composition hereinafter set forth is believed to be essential in order to obtain the depilatory stick compositions of the present invention in suitable form. That is to say, a stick which is soft enough to react readily when applied to the wetted skin yet sufficiently hard to provide a stick product which exhibits good shelf life and other stability characteristics.

The present invention is disclosed in further detail by means of the following examples which are provided for the purpose of illustration only. It will be readily understood by those skilled in the art that various modifications in materials, quantities of materials, operating conditions, etc., can be made within the general disclosure of this application without departing from the spirit of the invention herein disclosed.

EXAMPLES

Compositions containing the following ingredients in the indicated percentages by weight were prepared:

| Ingredients | Example 1 | Example 2 |
|---|---|---|
| Deionized water | 30.0 | 42.0 |
| Calcium thioglycolate | 6.5 | 6.0 |
| Sodium Stearate | 9.0 | 9.0 |
| Propylene Glycol | 44.5 | 33.0 |
| Sodium hydroxide 50% solu. | 10.0 | 10.0 |
|  | 100.0 | 100.0 |
| pH of 10% Solu. in water | 12.35 | 12.30 |

The foregoing examples were prepared as follows:
Diffuse calcium thioglycolate into water followed by the addition of a propylene glycol aqueous dispersion. Sodium hydroxide solution (50%) is added and the batch mixed until all components are dispersed and suspended (a gel like consistency will form). The batch is then heated to 70° C.-82° C. +/−5° while mixing When thoroughly mixed, while maintaining the temperature at about 82° C. +/−2° C. sodium stearate is added into the hot mix and stirred until all ingredients are thoroughly dispersed. The mixture is cooled to 70° C. +/−2° C. and poured into containers and allowed to cool and solidify at room temperature 20° C.-25° C. before use.

The stick was dipped in water and applied to the wet hairy surface of a human forearm with a circular motion. The rubbing action with the stick stick on the wetted skin produces a thin lotion, i.e., about a 10% aqueous solution that depilates the hair in less than 10 minutes. This thin lotion which forms on the skin may be slightly rubbed again with the moistened stick until all hair is removed.

Example 3

A transparent depilatory stick composition having the following composition was prepared:

| Ingredients | % W/W |
|---|---|
| Deionized water | 30.0 |
| Thioglycolic Acid 80% (Evans) | 5.0 |
| Sodium Hydroxide (50% solu.) | 12.0 |
| BRIJ 30 (ICI) | 3.0 |
| Propylene Glycol | 42.0 |
| Sodium Stearate C-7 (wites) | 8.0 |
|  | 100.0 |
| pH of 10% Solution in water | (12.07) |

The composition was prepared as follows:
Thioglycolic acid is dissolved in water and sodium hydroxide is added and the batch mixed until all ingredients are dispersed. Heating to 70° C. is started and propylene glycol dispersion in water is added with mixing followed by the addition of BRIJ 30 with mixing continued until all ingredients are dispersed. While mixing, the batch is heated to 82° C. +/−5° and sodium stearate is added and mixing continued until all ingredients are dispersed. The batch is then poured into containers hot (75° C. +/−2° C.) and allowed to cool to room temperature 25° C.-25° C. before use.

As with the preceeding examples, the stick was applied to a wet hairy surface with a circular motion. A thin lotion is produced that depilates the hair in less than 10 minutes. This thin lotion which forms on the skin could be slightly rubbed again with the moistened stick until all hair is removed.

What is claimed is:
1. Hydrous stick depilatory compositions consisting essentially of from about 6% to about 12% by weight sodium stearate, from about 15% to about 60% by weight propylene glycol, from about 4% to about 8% by weight of a thioglycolate acid salt selected from the group consisting of sodium, calcium and potassium thioglycolate and mixtures thereof and from about 15% to about 60% by weight water.

2. Hydrous stick depilatory compositions as claimed in claim 1 containing from about 33% to about 45% by propylene glycol, from about 5% to about 6.5% by weight calcium thioglycolate; from about 27% to about 42% by weight water and about 9% by sodium stearate.

3. A method of depilating hair from the skin which comprises moistening the skin surface with water and rubbing said surface with the hydrous stick compositions of claims 1 or 2 which have previously been dipped in water whereby a thin depilating lotion is formed and allowing said lotion to depilate the hair on the skin's surface.

* * * * *